(12) United States Patent  
Cohen

(10) Patent No.: US 6,712,795 B1
(45) Date of Patent: Mar. 30, 2004

(54) SURGICAL PROCEDURE AND APPARATUS

(76) Inventor: Lester Cohen, 737 Park Ave., New York City, NY (US) 10021

( * ) Notice: Subject to any disclaimer, the term of this patent is extended or adjusted under 35 U.S.C. 154(b) by 0 days.

(21) Appl. No.: 10/165,473

(22) Filed: Jun. 7, 2002

(51) Int. Cl.7 .......................... A61B 17/04; A61M 37/00

(52) U.S. Cl. .......................................... 604/233; 604/26

(58) Field of Search ................................ 600/201, 210, 600/227, 231, 232, 233; 604/26

(56) References Cited

U.S. PATENT DOCUMENTS

| | | | |
|---|---|---|---|
| 5,407,427 A | * | 4/1995 | Zhu et al. ...................... 604/26 |
| 5,503,617 A | | 4/1996 | Jako ............................ 600/201 |
| 5,573,495 A | | 11/1996 | Adler ........................... 600/204 |
| 5,957,902 A | * | 9/1999 | Teves ........................... 604/264 |
| 6,224,545 B1 | | 5/2001 | Cocchia et al. ............... 600/233 |
| 6,309,382 B1 | * | 10/2001 | Garrison et al. ............... 606/1 |
| 6,371,964 B1 | * | 4/2002 | Vargas et al. ................. 606/153 |

OTHER PUBLICATIONS

"Surgical Devices Since 1969"–Title. Brochure Published 1997 By Mediflex, Islandia, NY.

* cited by examiner

Primary Examiner—Pedro Philogene
Assistant Examiner—David A Bonderer
(74) Attorney, Agent, or Firm—Robert W. J. Usher

(57) ABSTRACT

Adjustable body penetrating blades of a min-retractor are inserted, closed together, into a small incision in an abdominal cavity, spread to widen the incision and a trocar tube is installed in the cavity by clamping between the blades enabling performance of a laparoscopic procedure in conjunction with other trocars inserted into other incisions. Rapid reversal of the laparoscopic procedure is achieved by moving the blades apart, releasing the trocar, and swinging distal ends of the blades apart expanding an inner operating window. A stand having a flexible positioning arm attached to the min-applicator maintains the min-retractor elevated after withdrawal of the trocar and loss of pneumoperitoneum pressure from insufflation. The blades of the mini-retractor gripping the tube of the trocar define between them a scalpel access opening to skin on respective opposite sides enabling enlargement of the incision with the retractor and trocar installed in the abdominal cavity.

6 Claims, 4 Drawing Sheets

SURGICAL PROCEDURE AND APPARATUS

FIELD OF THE INVENTION

The invention relates to a surgical procedure which requires incision through the outer tissues of the body and to apparatus for implementing such procedure.

BACKGROUND OF THE INVENTION

There are several distinct invasive surgical procedures requiring incisions through the outer tissues of the body.

The most traditional approach, known as open surgery usually involves an incision of at least 10–12 inches, often as much as 14 inches, and is favored for providing a relatively large opening for direct visibility of the underlying tissue, easy access for surgical instruments and a surgeon fingers (palpability). A retractor having blades extending in side by side relation into the incision and movable apart to spread edges of the incised tissue is often used to increase the field of operation.

Disadvantages of the open procedure include a relatively long healing time significant bleeding and patient trauma. Nevertheless, open surgery remains by far the most widely used surgical approach.

In an attempt to obviate the above disadvantages, a minimally invasive procedure know as laparoscopy was developed. In laparoscopy, a ring of several, (usually four), small incisions, each of typically ¾ inch are made through outer tissue, such as the abdominal wall and tubes of various stick-like instruments (trocars), incorporating endoscopes/cameras, illuminating devices and insufflation cannula, are inserted therein. The abdominal wall is raised away from underlying tissue by the insufflation pressure, exposing the underlying tissue for access and visibility so that the entire operation can be performed on camera using the inserted instruments.

However, approximately 15–20% of laparoscopic procedures, must be reversed to open surgery for various reasons, such as discovery of extensive disease, or camera blocking events such as excessive bleeding, which can be difficult to locate and staunch in a closed environment, or leakage of other body fluids. Such reversals can be traumatic, requiring the steps of withdrawal of the trocars with loss of insulation pressure, radical extension of one or more of the incisions and fitting a retractor into the newly extended incision, all of which must be carried out with a high degree of urgency under pressure and are undesirably time consuming, with significant additional loss of blood often resulting in significantly greater patient risk than if the traditional approach of open surgery had been adopted initially.

Notwithstanding, the apparent advantages of minimal invasion, it is believed that laparoscopy is used in only approximately 15% of all invasive surgical procedures, most commonly for removal of the gall bladder (for which the procedure was originally devised).

A third ,most recent, approach to invasive surgery described and claimed in my U.S. Pat. No. 6,224,545, issued May 1, 2001, the disclosure of which is incorporated herein by reference, utilizes a special mini-retractor which permits surgery through an outer incision, i.e., outer operating window, much smaller than that required by the traditional open surgery approach, while providing a field of operation within the patient's body, i.e., inner operating window, which is much larger than the outer operating window and, in such respect, provides much of the access advantage of the traditional approach of open surgery.

Such mini-retractor, (trademark 'DirecTrac'), comprises a pair of blades having proximal ends and distal ends inserted through the incision into the body, the proximal ends being pivotally mounted in side by side relation on a frame both for translational movement apart to expand the outer operating window and for swiveling movement to spread (fan) the distal ends within the body thereby to expand the inner operating window.

As a result of the ability to spread the distal end of the blades an inner operating window (access) of as much as 7–10 inches can be obtained from an incision of only 2–4 inches, which is much smaller than that required for open surgery, while the requirement for insufflation is obviated. In addition, angulation or tilting the device in opposite directions may further increase the transient field of view to as much as much as possibly 14–20 inches creating a relatively open environment as compared with conventional laparoscopy. Notwithstanding, this procedure remains a different and distinct approach from laparoscopy.

SUMMARY OF THE INVENTION

It is an object of the invention to provide a surgical procedure which enjoys most of the advantages of a conventional laparoscopic procedure in requiring only a relatively small increase in initial incision size, but which ameliorates disadvantages associated with of reversal of the conventional laparoscopic procedure in avoiding a need for open surgery and associated delays, blood loss and trauma.

The invention utilizes a mini-applicator similar to the type described above but having blades with narrower sidewalls, permitting the access incision or outer operating window to be as small as 1–1.5 inches.

According to one aspect, the invention provides the steps of: making a small incision of 1–1.5 inches in length in the abdominal wall; providing a mini-retractor with blades having adjacent trocar engaging sidewalls of arcuate cross-section conforming with an outer profile of a tube of a trocar; inserting the blades in closed together, substantially parallel relation, into the incision into the abdominal cavity; moving the blades a small distance apart and inserting a tube of a trocar axially between the blade sidewalls into the abdominal cavity and closing the blades together to embrace the cylindrical tube of the trocar in a sealing fit thereby mounting the trocar in the cavity; and, performing a laparoscopic procedure.

If reversal of the laparoscopic procedure is needed it is only necessary to relax the blades, permitting axial withdrawal of the trocar from the mini-retractor and to swivel (pivot or swing) the distal ends of the blades apart to enlarge the inner operating window.

Although the sealing fit between the blades and the tube of the trocar and surrounding tissue should usually be sufficient to maintain pneumoperitoneum pressure by insufflation, an auxiliary abdominal wall elevator may be employed. For example, the abdominal wall elevator described in U.S. Pat. No. 5,573,495 to Adler may be inserted through another trocar, to reduce the pneumoperitoneum pressure required for adequate access inside the abdominal cavity.

Thus, the procedure of the invention often obviates the need to greatly enlarge the incision and the manipulative steps otherwise required to seat a retractor in an enlarged incision, saving valuable time, blood loss and trauma.

An abdominal elevator and flexible arm positioner comprising a stand normally clamped to the operating table and supporting a flexible positioning arm with a clamping head which can be clamped to the min-retractor can also be used to maintained the mini-retractor elevated when the trocar is removed. Preferably, the abdominal wall elevator and positioner is clamped to the mini-retractor as soon as practicable after the trocar has been clamped in the mini-applicator so that the min-retractor is in place, ready for use to maintained elevation of the abdominal wall in the event of reversal involving removal of the trocar and, in consequence, loss of pneuomoperitoneum pressure.

Preferably, when the trocar tube is clamped between the blades of the mini-applicator, small, instrument access gaps are defined between the proximal ends of the blades on respective opposite sides of the trocar tube at the location of entry, exposing surface portions of skin at opposite edges of the incision to enable a surgeon to increase the length of the incision with the mini-retractor still in place by simply inserting scalpel or other suitable instrument into the gaps. The proximal ends of the blades are then moved apart to spread apart the edges of the enlarged incision to the fullest extend and therefore increase the outer operating window.

An enlargement of the incision to approximately 3.5–5 inches, whilst significantly less than the size required for traditional open surgery, provides an incision with an outer operating window of sufficient size for insertion of a surgeon's fingers and for the palpability, much sought after by many surgeons, while the inner operating window which has been already increased in constant size by fanning the distal ends of the blades can be further increased by subsequent angulation or tilting of the retractor alternately in opposite directions, enabled by flexure of the positioning arm to provide a much larger transient field of view. Even, an outer operating window of approximately 1.5 inches, providing a constant inner operating window increased to approximately 7 inches by the pivotal leg fanning or spreading, can result in an inner transient window of approximately 14 inches as a result of tilting the retractor. Thus, increasing the size of the incision by 3 inches, for example, of will also increase the constant inner operating window to 10 inches while tilting can increase the transient size of the inner window to as much as 20 inches creating, on reversal, an open operating environment comparable in many respects to open surgery.

According to another aspect, the invention provides a surgical apparatus comprising, in combination, a mini-retractor of the kind described above having blades with adjacent, arcuate, trocar clamping sidewalls and a trocar clamped in a sealing fit between opposed sidewalls of the blades.

BRIEF DESCRIPTION OF THE DRAWINGS

In order that the invention may be readily understood, specific embodiments thereof will now be described, by way of example only and with reference to the accompanying drawings in which.

DESCRIPTION OF PARTICULAR EMBODIMENTS

Figure 1:
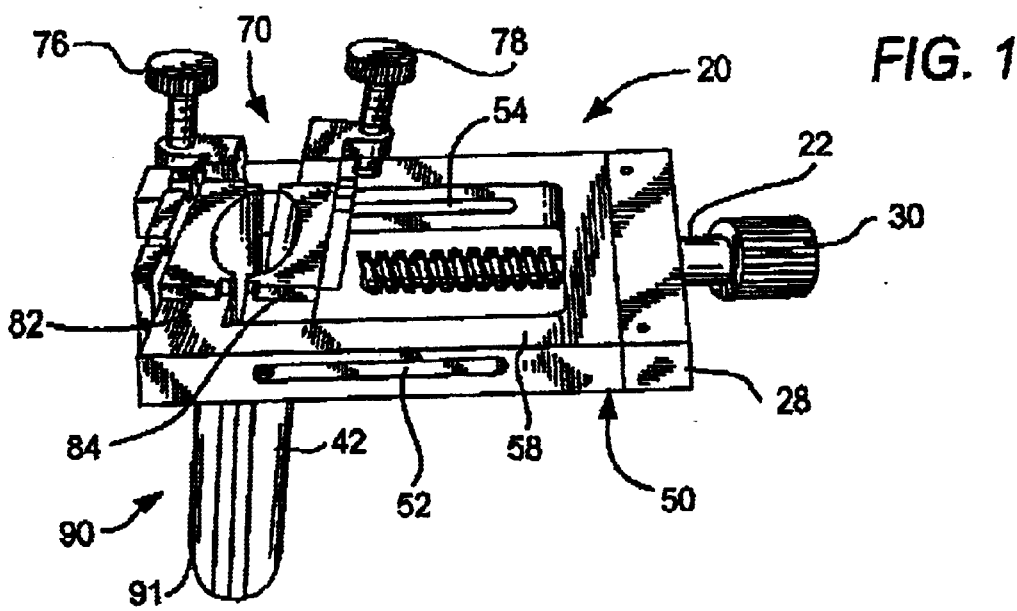
FIG. 1 is a copy of a photograph of a view of a mini-retractor of a same type as that employed in the invention, in a closed position.
Figure 2:
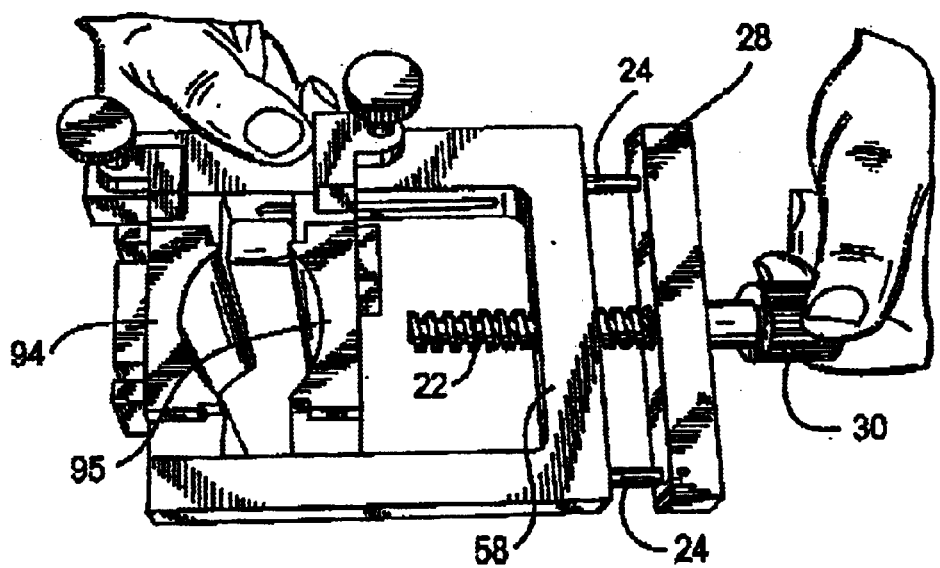
FIG. 2 is a copy of a photograph of the mini-retractor of FIG. 1 being opened.
Figure 3:
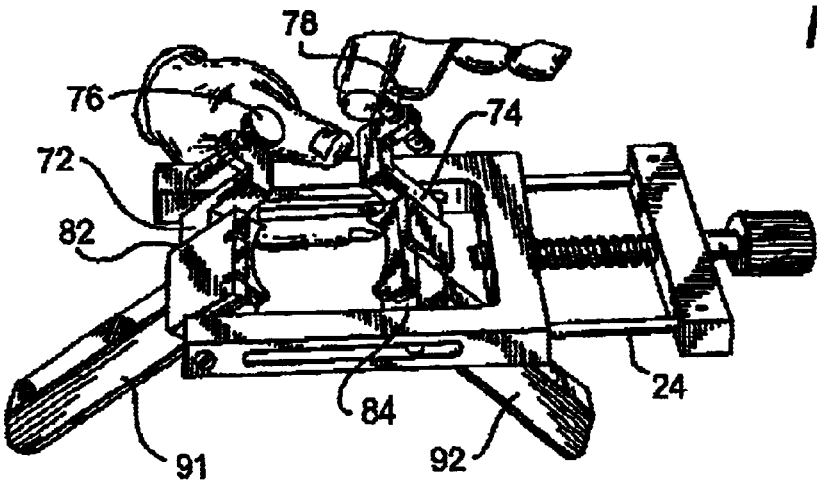
FIG. 3 is a copy of a photograph of the mini-retractor of FIG. 1 in an open position with both blades angled outwardly to form a reverse funnel or tent.

A surgical retractor 10 similar to that employed in the invention is illustrated in FIGS. 1–3 is disclosed in U.S. Pat. No. 6,224,545 and comprises a thread assembly 20, a U-shape rack assembly 50, a swivel assembly 70, and removable blade assembly 90.

As detailed in the prior patent, the thread assembly 20 comprises a crosspiece 28 rotatively mounting rod 22 threaded in crosspiece 58 of the rack assembly 50 and traveler rods 24 slidably received in slots respective legs 52, 54 of the rack assembly. The swivel assembly 70 comprises first and second swivels 72, 74 with blade mounts 82, 84 holding respective blades 91, 92, and respectively mounted for pivotal movement, on cross pins, by adjustment of respective thumbscrews 76, 78, to free ends of respective legs 52, 54, and to the traveler rods 24.

As shown in FIG. 2, turning the knob 30 rotates threaded rod 22 within crosspiece 58 of the rack assembly produces longitudinal translational movement of the crosspiece 28 increasing the spacing between a proximal end 94 of first blade 91 and a proximal end 95 of second blade 92.

As shown in FIG. 3, screwing down thumbscrews 76,78 adjusts the angles of the first and second swivels and blades 91, 92 significantly increasing the separation of their distal ends and, therefore, the inner operating window.

Figure 4:
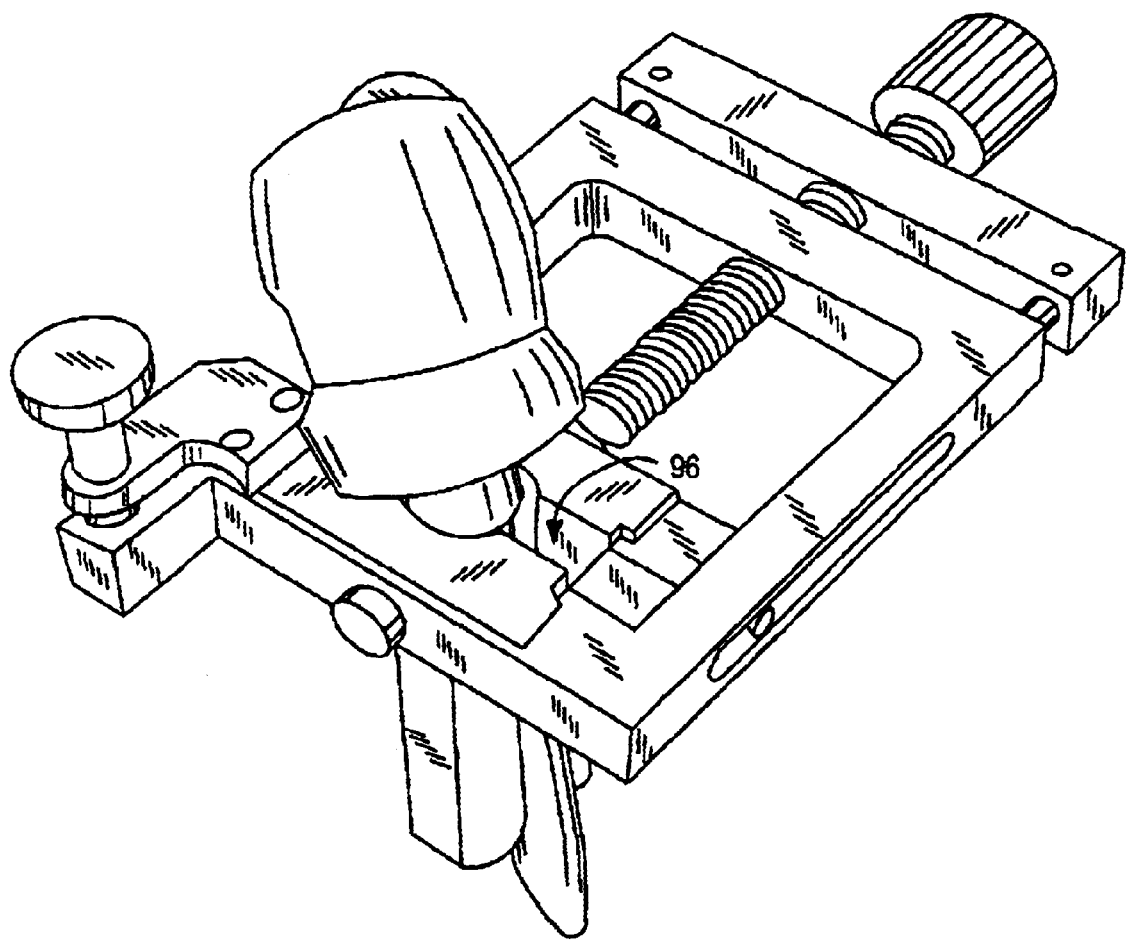
FIG. 4 is a copy of a photograph of a first type of trocar mounted in a mini-retractor, according to the invention.
Figure 5:
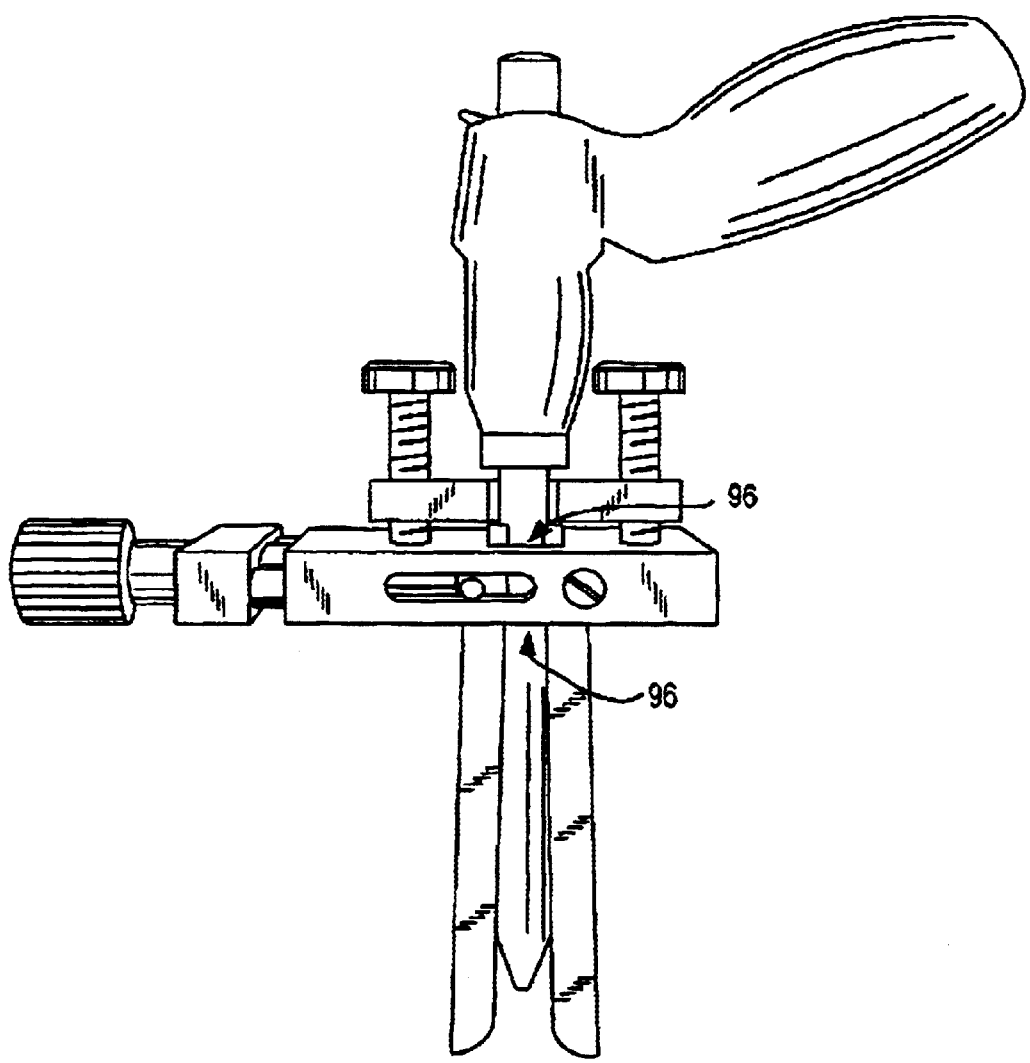
FIG. 5 is a copy of a photograph of a second type of trocar mounted in a mini-retractor according to the invention.

In the mini-retractor of the invention shown particularly in FIGS. 4 and 5, the blades have facing trocar engaging sidewalls approximately 1–1.5 inches wide ? and shaped to conform with the cylindrical outer profile of the trocar stem or tube.

In the procedure, a small incision approximately 1.5 inches long is made in the abdominal wall, the mini-retractor with the blades thereof closed together in substantially parallel relation is inserted into the incision so that the distal portions of the legs enter the abdominal cavity. The second blade is then moved a small distance apart from the first blade by turning the knob. The tube of a suitable trocar is then inserted between the blades into the abdominal cavity and the knob turned in the reverse direction to close the blades together to embrace the trocar tightly in a sealing fit sufficient, in situ, to maintain pneumoperitoneum pressure by insufflation, at least when employed in conjunction with an auxiliary device such as an auxiliary abdominal wall elevator.

A laparoscopic type procedure is then performed in association with other trocars inserted in other incisions in conventional manner.

When reversal is needed, it is only necessary to relax the blades of the min-retractor which is already positioned in the incision, permitting removal of the trocar and to pivot or swing the distal ends of the blades apart to enlarge the inner operating window.

Thus, the procedure of the invention obviates need to enlarge the incision and subsequently to handle and seat a retractor in the enlarged incision, saving valuable time, blood loss and trauma.

It will be noted from FIG. 4 that the opposed surfaces of the proximal ends of the blades do not close completely together when clamping the trocar but are designed to define between them small gaps or scalpel access openings 96 to portions of the skin surface on respective opposite sides of the incision. This enables a surgeon to increase the length of the incision with the mini-retractor applicator still in place in the incision by simply inserting scalpel or other suitable instrument into the gaps. The proximal ends of the blades are then moved apart to spread apart the edges of the incision to the fullest extend and therefore increase the outer operating window.

An enlargement of the incision to approximately 3.5–5 inches, whilst significantly less than the size required for traditional open surgery, provides an incision with an outer operating window of sufficient size for insertion of a surgeon's fingers and for the palpability, much sought after by many surgeons, while the inner operating window which has been already increased in constant size by fanning the distal ends of the blades can be further increased by subsequent angulation or tilting of the retractor enabled by flexure of the positioning arm to provide a much larger transient field of view. Even, an outer operating window of approximately 1.5 inches, providing a constant inner operating window increased to approximately 7 inches by the pivotal leg spreading, can result in an inner transient window of approximately 14 inches as a result of tilting the retractor. Thus, increasing the size of the incision by 3 inches, for example, of will also increase the constant inner operating window to 10 inches while tilting can increase the transient size of the inner window to as much as 20 inches thereby creating, on reversal, an open operating environment comparable in many respects to open surgery.

Thus, even if enlargement of the incision (within limits) is required, there is no need to remove and reseat the min-retractor in the incision, saving valuable time and risk to the patient.

Figure 6:
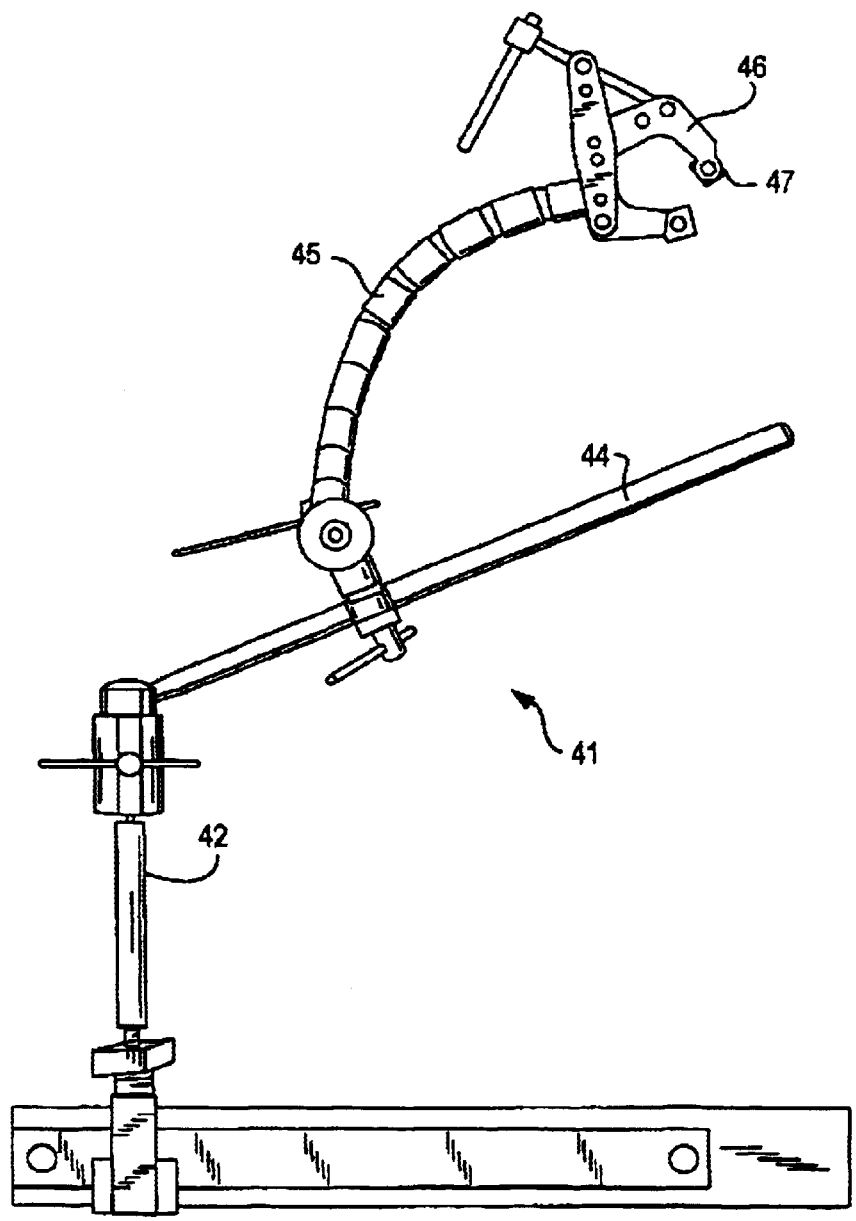
FIG. 6 is a copy of a photograph of an abdominal wall elevator and positioner.

An abdominal wall elevator and positioner 41 similar to that shown in FIG. 6 comprises a stand 42 clamped to an operating table 43 with an upper end and supporting a horizontal rod 44 at a selected angle and height and a flexible positioning arm 45 having an adjustable clamp mechanism 46 at a free end for attachment to the min-retractor after installation of the trocar therein. The adjustable clamp mechanism is generic and many different forms can be used to adapt to various retractors. The pointed ends of the pincer-form jaws 47 can engage in the slots at a location between the blades.

In a modification, the clamping head bridges the min-applicator and has jaws gripping opposite sides of legs of the rack assembly 50.

The abdominal wall elevator and positioner 41 is used to maintained the retractor elevated when the trocar is removed and is clamped at the location of the slots, between the blades, immediately after clamping the trocar in place. Flexure of the positioning arm permits the angulation or tilting of the retractor after the distal ends of the legs have been fanned apart.

Although the combination of min-retractor and trocar will usually provide a sufficient seal to maintain insulation pressure, an additional abdominal wall elevator inserted through a trocar such as that taught in U.S. Pat. No. 5,573,495, issued to Adler in 1996, can be used to permit lower pressure pneumoperitoneum pressure helping to compensate for any pressure loss arising from minor leakage.

Both abdomiinal wall elevators described above are made by MEDIFLEX division of FLEXBAR MACHINE Corp. of Islandia, N.Y.

What is claimed is:

1. A surgical procedure comprising the steps of:

providing a trocar having a cylindrical body penetrating tube;

providing a mini-retractor comprising a pair of blades for insertion through an incision into the body and having proximal ends and distal ends and, frame means mounting the proximal ends both for translational movement of the blades relatively together and apart to expand an outer operating window and for relative pivotal movement to fan the distal ends within the body to expand an inner operating window, the blades having adjacent, trocar engaging sidewalls arcuately shaped to conform with the outer profile of the trocar;

making a plurality of small incisions in an abdominal wall, inserting the blades of the retractor with the blades thereof closed together in side by side substantially parallel relation through a selected incision into the abdominal cavity;

relatively moving the blades a small distance apart;

inserting a cylindrical tube of a trocar between the blades into the abdominal cavity;

moving the blades together into clamping engagement with the tube of the trocar in a sealing fit, thereby mounting the trocar in the Incision;

inserting trocars in other incisions;

inflating the abdominal cavity by insufflation through a trocar other than the trocar inserted in the min-retractor to provide pneumoperitoneum pressure and to elevate the min-retractor and, performing at least an initial part of a laparoscopic surgical procedure using the trocar in conjunction with trocars inserted in other incisions.

2. A surgical procedure according to claim 1, comprising the further steps of:

reversing the laparoscopic procedure after the performance of the initial part by moving the blades relatively apart to release the trocar therein;

withdrawing the tube of the trocar axially from between the blades; and, swinging the distal ends of the blades apart to enlarge the inner operating window.

3. A surgical procedure according to claim 2, comprising the further steps of:

providing a stand mounted on an operating table, the stand having a flexible positioning arm and attaching the flexible positioning arm to the mini-retractor to maintain the min-retractor in an elevated position after withdrawal of the trocar.

4. A surgical procedure according to claim 2, wherein the blades of the mini-retractor gripping the tube of the trocar define between them an access opening for a scalpel to skin on respective opposite sides of tube of the incision and comprising the further steps of enlarging the incision by severing skin tissue between the blades of the mini-retractor on respective opposite sides of the incision.

5. A surgical procedure comprising the steps of:

providing a trocar having a cylindrical, body penetrating tube;

providing a mini-retractor comprising a pair of blades of 1–1.5 inches wide for insertion through an incision into the body and having proximal ends and distal ends and, a frame;

means mounting the blades on the frame for translational movement of proximal ends between stable positions in which the proximal ends are adjacent and apart to expand an outer operating window and for manually operable pivotal movement between stable positions in which the blades extend in parallel relation and with distal ends fanned apart to expand an inner operating window;

the blades having adjacent, trocar engaging sidewalls at proximal ends, arcuately shaped to conform with the outer profile of the trocar;

making a plurality of small incisions in an abdominal wall, a selected incision being 1–1.5 inches long, inserting the blades of the retractor with the blades thereof closed together in side by side (substantially parallel) relation through the selected incision into the abdominal cavity;

relatively moving the blades a small distance apart;

inserting a cylindrical tube of a trocar between the blades into the abdominal cavity;

moving the blades together into clamping engagement with the tube of the trocar in a sealing fit, thereby mounting the trocar in the incision;

inserting trocars in other incisions;

inflating the abdominal cavity by insulation through a trocar other than the trocar inserted in the min-retractor to provide pneumoperitoneum pressure and to elevate the min-retractor and, performing at least an initial part of a laparoscopic surgical procedure using the trocar in conjunction with trocars inserted in other incisions.

6. A surgical procedure according to claim 5, comprising the further steps of:

reversing the laparoscopic procedure after the performance of the initial part by moving the blades relatively apart to release the trocar therein;

withdrawing the tube of the trocar axially from between the blades; and, swinging the distal ends of the blades apart to enlarge the inner operating window to at least 7 inches.

* * * * *